(12) United States Patent
Ahman et al.

(10) Patent No.: US 6,734,303 B2
(45) Date of Patent: May 11, 2004

(54) PROCESS FOR THE PRODUCTION OF QUINAZOLINES

(75) Inventors: Jens Bertil Ahman, Sandwich (GB); Paul Blaise Hodgson, Sandwich (GB); Sarah Jane Lewandowski, Sandwich (GB); Robert Walton, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/144,337

(22) Filed: May 13, 2002

(65) Prior Publication Data

US 2003/0004339 A1 Jan. 2, 2003

Related U.S. Application Data

(60) Provisional application No. 60/301,750, filed on Jun. 28, 2001.

(30) Foreign Application Priority Data

May 18, 2001 (GB) .............................................. 0112061

(51) Int. Cl.[7] .............................................. C07D 401/14
(52) U.S. Cl. ...................................... 544/283; 544/284
(58) Field of Search ................................. 544/283, 284

(56) References Cited

U.S. PATENT DOCUMENTS 4,758,568 A    7/1988    Campbell et al. ........... 514/254

FOREIGN PATENT DOCUMENTS

| WO | WO 9723462 |    | 7/1997 |
|----|------------|----|--------|
| WO | WO 9830560 |    | 7/1998 |
| WO | WO 98/50370 | *  | 11/1998 |

* cited by examiner

*Primary Examiner*—Deepak Rao
(74) *Attorney, Agent, or Firm*—Peter C. Richardson; Gregg C. Benson; Carl J. Goddard

(57) ABSTRACT

The invention provides a process for the production of a compound of formula (A) or a pharmaceutically acceptable salt or solvate thereof:

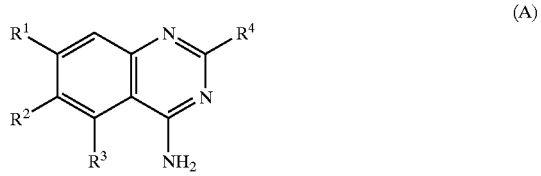

(A)

which comprises condensing a compound of formula (B)

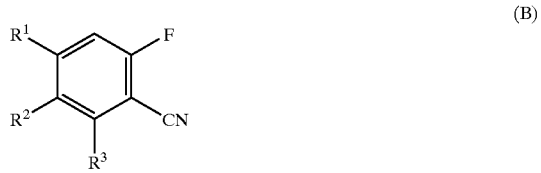

(B)

with a compound of formula (C):

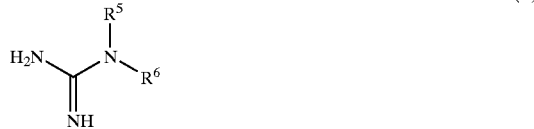

(C)

Compounds of formula (A) are useful in the treatment of benign prostatic hyperplasia.

15 Claims, No Drawings

PROCESS FOR THE PRODUCTION OF QUINAZOLINES

BACKGROUND OF THE INVENTION

The present application claims the benefit of U.S. Provisional Patent Application Serial No. 60/301,750, filed Jun. 28, 2001, the contents of which are hereby incorporated by reference.

The present invention relates to a novel process for producing quinazoline compounds that are useful in therapy. More specifically, the compounds are useful in the treatment of benign prostatic hyperplasia.

International Patent Application WO 98/30560 discloses a number of substituted quinoline and quinazoline compounds of formula (I), and their pharmaceutically acceptable salts, which are indicated in the treatment of benign prostatic hyperplasia:

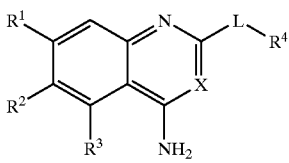

wherein $R^1$ represents $C_{1-4}$ alkoxy optionally substituted by one or more fluorine atoms;

$R^2$ represents H or $C_{1-6}$ alkoxy optionally substituted by one or more fluorine atoms;

$R^3$ represents a 5- or 6-membered heterocyclic ring containing at least one heteroatom selected from N, O and S, the ring being optionally substituted by one or more groups selected from halogen, $C_{1-4}$ alkoxy, $C_{1-4}$ alkyl and $CF_3$;

$R^4$ represents a 4-, 5-, 6-, or 7-membered heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, $C_{1-4}$ alkyl, $C_{1-4}$ alkoxy, halogen, $CONR^8R^9$, $SO_2NR^8R^9$, $(CH_2)_bNR^8R^9$ and $NHSO_2(C_{1-4}$ alkyl), and when S is a member of the ring system, it may be substituted by one or two oxygen atoms;

$R^8$ and $R^9$ independently represent H or $C_{1-4}$ alkyl, or together with the N atom to which they are attached they may represent a 5- or 6-membered heterocyclic ring containing at least one heteroatom selected from N, O and S;

b represents 0, 1, 2 or 3;

X represents CH or N; and

L is absent, or represents a cyclic group of formula Ia,

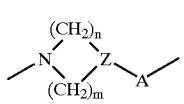

in which N is attached to the 2-position of the quinoline or quinazoline ring;

A is absent or represents CO or $SO_2$;

Z represents CH or N;

m represents 1 or 2, and in addition, when Z represents CH, it may represent 0; and n represents 1, 2 or 3, provided that the sum of m and n is 2, 3, 4 or 5;

or represents a chain of formula Ib,

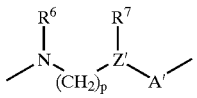

in which N is attached to the 2-position of the quinoline or quinazoline ring;

A' and Z' have the same significance as A and Z above, respectively;

$R^6$ and $R^7$ independently represent H or $C_{1-4}$ alkyl; and p represents 1, 2 or 3, and in addition, when Z' represents CH, it may represent 0.

The compounds of formula (I) in which X=N and L is absent are of particular interest. Of these compounds, 4-amino-2-(5-methanesulfonamido-1,2,3,4-tetrahydroisoquinol-2-yl)-6,7-dimethoxy-5-(2-pyridyl)quinazoline is of special interest.

According to WO 98/30560, the compounds of formula (I) can be produced by a number of processes. However, none of these processes involves the condensation of the two main parts of the molecule in a convergent synthesis and each process suffers disadvantages. For example, 4-amino-2-(5-methanesulfonamido-1,2,3,4-tetrahydroisoquinol-2-yl)-6,7-dimethoxy-5-(2-pyridyl)quinazoline (the compound of Example 19 in WO 98/30560) is prepared according to the following scheme:

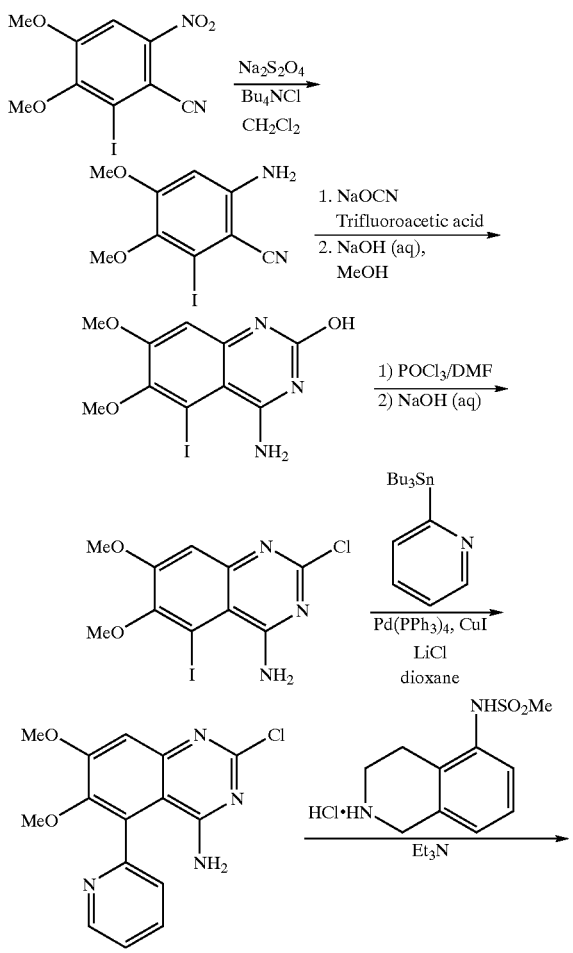

-continued

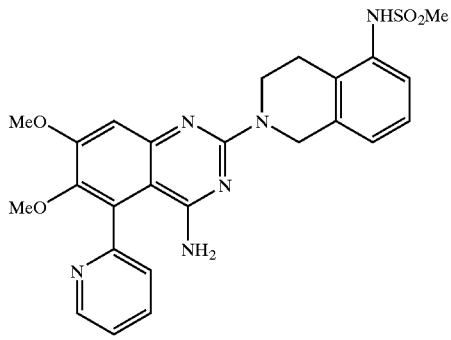

The routes described in WO 98/30560 suffer the disadvantage that they involve the use of tributyl stannyl pyridine in combination with copper iodide and tetrakis (triphenylphosphine) palladium. One problem of this route is that the tributyl stannyl pyridine is expensive to purchase. The compound is toxic and there are issues of worker safety and concerning the environment. After use, spent reactants are difficult and expensive to dispose of because of the adverse effects organotin compounds have on their surroundings. A further problem with the prior art process is its lack of convergency. A number of synthetic steps are required to produce the quinazoline compounds in the disclosed processes, with each synthetic step leading both to a reduction in yield and increasing the possibility of competing side reactions. Thus the conventional reaction requires effort to purify the product and may not give an optimal yield.

A further problem with the prior art process of WO 98/30560 is that large pebble-like aggregates are formed in the reactor during the reaction. The identity of these aggregates is not clear but they are believed to be formed of inorganic material derived from the various inorganic additives used during the reaction such as lithium chloride and copper iodide. In this process, there is the risk that the pebble-like aggregates could crack the reactor causing leakage of the reaction medium and the hazard of fire or poisoning. At the very least there is the problem that the reaction leads to scratching of the interior of the reaction vessel thus causing premature wearing of the vessel, poor heat dissipation in the mixture or blocking.

It is an aim of the present invention to provide a synthetically efficient process for the production of quinazoline derivatives which avoids the problems of the prior art process. It is also an aim to provide a process in which the convergency (ie the bringing together of synthetic fragments) is maximised. It is thus an aim to provide a route to the compounds of formula (I), which offers an improved yield relative to the existing routes. It is a further aim of the process of the present invention to avoid the use of organotin compounds on account of their hazardous nature. It is a further aim of the present invention to provide a process, which minimizes the number of synthetic steps required and which avoids the problem of competing reactions and/or the disposal of hazardous materials.

SUMMARY OF THE INVENTION

Accordingly, the present inventors have now found an improved route to the preferred quinazoline derivatives of formula (I) above which overcomes many of the disadvantages of the prior art.

According to the present invention, there is provided a process for the production of a compound of formula (A) or a pharmaceutically acceptable salt or solvate thereof:

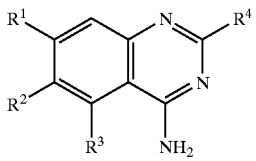
(A)

wherein:
$R^1$ represents $C_{1-4}$ alkoxy optionally substituted by one or more fluorine atoms;
$R^2$ represents H or $C_{1-6}$ alkoxy optionally substituted by one or more fluorine atoms;
$R^3$ represents a 5- or 6-membered heterocyclic ring containing at least one heteroatom selected from N, O and S, the ring being optionally substituted by one or more groups selected from halogen, $C_{1-4}$ alkoxy, $C_{1-4}$ alkyl and $CF_3$;
$R^4$ is a 4-, 5-, 6-, or 7-membered heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, $C_{1-4}$ alkyl, $C_{1-4}$ alkoxy, halogen, $CONR^8R^9$, $SO_2NR^8R^9$, $(CH_2)_bNR^8R^9$ and $NHSO_2$ $(C_{1-4}$ alkyl), and when S is a member of the ring system, it may be substituted by 1 or 2 oxygen atoms;
the process comprising condensing a compound of formula (B)

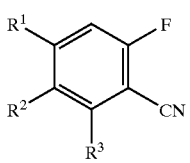
(B)

wherein
$R^1$ to $R^3$ are as defined above;
with a compound of formula (C):

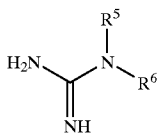
(C)

wherein
$R^5$ and $R^6$ taken together with the N atom to which they are attached represent a 4-, 5-, 6-, or 7-membered N-containing heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, $C_{1-4}$ alkyl, $C_{1-4}$ alkoxy, halogen, $CONR^8R^9$, $SO_2NR^8R^9$, $(CH_2)_bNR^8R^9$ and $NHSO_2(C_{1-4}$ alkyl), and when S is a member of the ring system, it may be substituted by 1 or 2 oxygen atoms;
$R^8$ and $R^9$ independently represent H or $C_{1-4}$ alkyl, or together with the N atom to which they are attached they may represent a 5- or 6-membered heterocyclic ring containing at least one heteroatom selected from N, O and S; and b represents 0, 1, 2 or 3;

and where necessary or desired, converting the resulting compound of formula (I) into a pharmaceutically acceptable salt or solvate, or converting the resulting salt or solvate into a compound of formula (I).

Preferably $R^1$ represents methoxy.

Preferably $R^2$ represents methoxy.

Preferably $R^3$ represents an aromatic heterocyclic ring. More preferably, $R^3$ represents pyridinyl, pyrimidinyl, thienyl, furanyl or oxazolyl. Most preferably $R^3$ represents 2-pyridinyl or 2-pyrimidinyl, the former being especially preferred.

Preferably $R^4$ represents a saturated 6-membered N-containing ring which is fused to an optionally substituted benzene or pyridine ring. More preferably, $R^4$ represents a tetrahydroisoquinoline ring system which is optionally substituted. Most preferably, $R^4$ is 5-methylsulfonylaminotetrahydroisoquinoline.

Most preferably, the process is used to prepare 4-amino-2-(5-methanesulfonamido-1,2,3,4-tetrahydroisoquinol-2-yl)-6,7-dimethoxy-5-(2-pyridyl)quinazoline.

Preferably the reaction is carried out in a polar aprotic solvent. The polar aprotic solvent is preferably dimethylsulfoxide.

Preferably the reaction is carried out in the presence of a base. More preferably, the base is an alkali metal carbonate. Most preferably, the base is caesium carbonate.

DETAILED DESCRIPTION OF THE INVENTION

Compounds of formula (C), as defined above, may be formed by reaction of a compound of formula (E), HCl.HR₄      (E)

wherein $R^4$ is as defined above,
with a compound of formula (F),

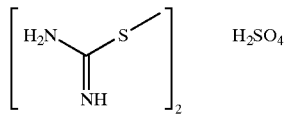      (F)

or a compound of formula (X),

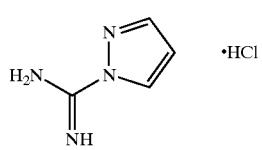      (X)

as described in Examples 2 and 2A below. Compounds of formula (E) may be prepared as described in WO 98/30560.

N-(2-amidino-1,2,3,4-tetrahydro-5-isoquinolyl) methanesulfonamide hydrochloride is of particular interest.

Preferably, the reaction is carried out in the presence of an aqueous base, such as aqueous sodium hydroxide; or an organic base, such as diisopropylethylamine.

In another aspect of the invention, there is provided a process wherein the compound of formula (B), as defined above, is formed by reaction of the compound of formula (D):

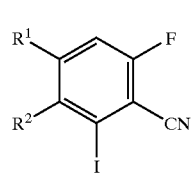      (D)

wherein $R^1$ and $R^2$ are as defined above;

with a pyridine derivative.

The pyridine derivative may be a pyridyl boronate. In this case, the reaction is preferably carried out in a polar aprotic solvent, such as dioxane. Preferably, the reaction is carried out at the reflux temperature of the solvent. Preferably, the reaction is carried out in the presence of a catalyst. More preferably, the catalyst is a palladium (0) catalyst. The pyridyl boronate may be used "damp" in the reaction, for example, it may be used when 50% "wet" with THF and dioxane.

A pyridyl boronate of particular interest is obtainable by reacting 2-bromopyridine with triisopropylborate in a solvent such as THF in the presence of a base such as n-butyllithium [see Examples 1(b) and 1A(a) below]. This pyridyl boronate is not readily analyzed. However, it is thought that its structure is as follows:

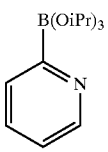

Alternatively, the compound of formula (D) is treated initially with zinc to produce a species containing a —Zn—I group (known as a "zincate"). In this case, the preferred pyridine derivative is a bromopyridine, for example 2-bromopyridine. In this case, the reaction is preferably carried out in a solvent such as THF. Preferably, the activation step and the reaction are carried out above room temperature. Preferably, the reaction is carried out in the presence of a catalyst. More preferably, the catalyst is a palladium (II) catalyst.

Most preferably, the process is used to prepare 6-fluoro-3,4-dimethoxy-2-(2-pyridyl)benzonitrile.

The invention further provides a process for the production of a compound of formula (A), as defined above, wherein the starting compound of formula (B) is prepared by methods also forming part of the invention.

The invention further provides the intermediate compounds of formulae (B) and (C), as defined above.

The invention is illustrated by the following examples. The following abbreviations may be used:

DCM=dichloromethane
DMF=dimethylformamide
DMSO=dimethylsulfoxide
mins=minutes
THF=tetrahydrofuran

EXAMPLE 1

6-Fluoro-3,4-dimethoxy-2-(2-pyridyl)benzonitrile (a) Preparation of 6-fluoro-2-iodo-3,4-dimethoxybenzonitrile

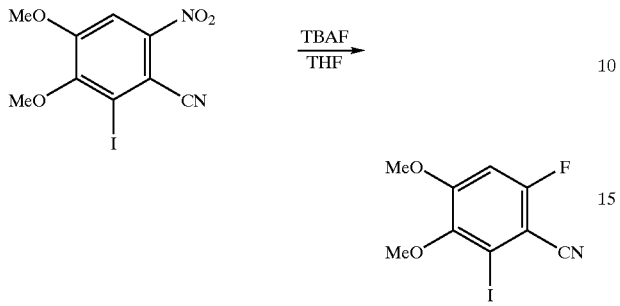

The 6-fluoro-2-iodo-3,4-dimethoxybenzonitrile is obtained from the corresponding 6-nitro-2-iodo-3,4-dimethoxybenzonitrile compound (prepared in Example 1 (d) of WO 98/30560) by reaction of the latter with an excess of tetrabutylammonium fluoride. 6-Nitro-2-iodo-3,4-dimethoxybenzonitrile (60 g) was slurried in dry THF (300 ml) at 0° C. under an atmosphere of nitrogen. A 5 molar excess of an aqueous solution of tetrabutylammonium fluoride was added slowly over a period of 20 minutes to the slurry and the temperature of the mixture was maintained below 5° C. The mixture was stirred at room temperature for a further 18 hours and then cooled to 0° C. Water (600 ml) was added slowly to the mixture which was maintained at a temperature below 5° C., followed by DCM (600 ml). The resulting phases were separated and the solvent was removed from the organic phase under reduced pressure to yield an oily residue. The oily residue was treated with methanol (210 ml) and allowed to stand overnight. The resulting solid was recovered from the methanol by filtration and dried to yield 27 g of the title compound as a solid. The solid was further purified by treating with methanol and allowing to stand overnight. The solid was recovered by filtration and drying to yield 23.2 g (42%) of the subtitle compound having HPLC purity of 92%.

(b) Preparation of the pyridyl boronate

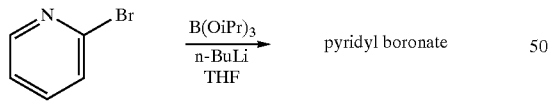

Under nitrogen, to a stirred, cooled (−30° C.) solution of 2-bromopyridine (5.0 g, 31.6 mmol) and triisopropylborate (5.95 g, 31.6 mmol) in anhydrous THF (50 ml) was added n-butyllithium (19.8 ml of a 1.6M solution in hexanes, 32 mmol) over 30 mins keeping the internal temperature in the range −20° C. to −15° C. The resulting brown suspension was left to stir for 1 hour in the temperature range −20° C. to −15° C. and then warmed to room temperature over 1 hour. The resulting suspension was filtered, the solid collected and dried in vacuo overnight at 45° C. The resulting pale brown solid (5.45 g) was assumed to be 31.6 mmol of the pyridyl boronate (i.e. the procedure had given a 100% yield).

(c) Preparation of 6-fluoro-3,4-dimethoxy-2-(2-pyridyl)benzonitrile

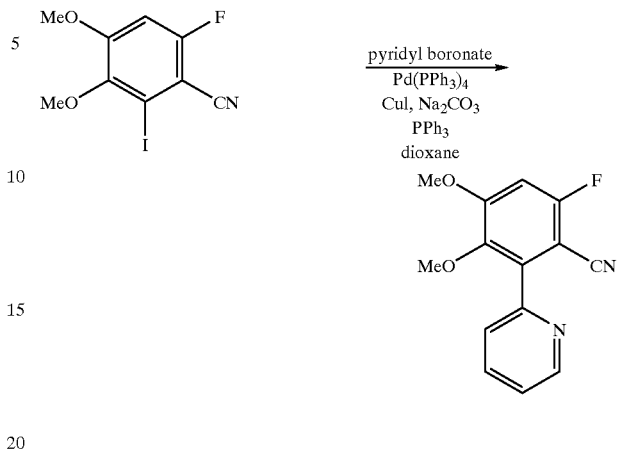

Under nitrogen, stirred dioxane (20 ml) at 80° C. was charged with 6-fluoro-2-iodo-3,4-dimethoxybenzonitrile from Example 1(a) (1.0 g, 3.3 mmol), tetrakis(triphenylphosphine) palladium(0) (0.19 g, 0.16 mmol), the pyridyl boronate from Example 1(b) (1.22 g, estimated to be 7.1 mmol), copper(I)iodide (0.25 g, 1.3 mmol), sodium carbonate (0.69 g, 6.5 mmol) and triphenylphosphine (0.17 g, 0.65 mmol) and the resulting brown slurry heated to reflux. Further portions of the pyridyl boronate were added at the following times after the reaction had reached reflux: 0.61 g after 30 mins; 0.61 g after 1 hour; 0.61 g after 1 hour 30 mins; 0.61 g after 2 hours 30 mins; 0.61 g after 3 hours; and 0.30 g after 4 hours. After a total of 5 hours at reflux the reaction was allowed to cool to room temperature, water (10 ml) and ethyl acetate (20 ml) were added and the resulting mixture allowed to stir for 15 mins. After this time, the mixture was filtered through Arbocel™ filter aid and the pad washed with ethyl acetate (20 ml). The phases were separated and the aqueous phase extracted with ethyl acetate (20 ml). The organic phases were combined and evaporated to a brown oil. Acetonitrile was added, the mixture warmed to reflux and left to cool to room temperature overnight. The resulting suspension was filtered to give a cream solid that was dried in vacuo overnight at 45° C. to give 0.42 g of the title product (49%).

EXAMPLE 1A

Second Route to 6-fluoro-3,4-dimethoxy-2-(2-pyridyl)benzonitrile (a) Preparation of the damp pyridyl boronate

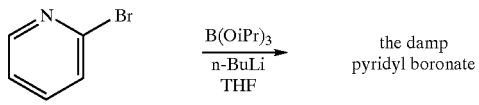

To a stirred solution of 2-bromopyridine (19.8 g, 125 mmol), and triisopropylborate (23.5 g) in anhydrous THF (198 ml) at −25° C. was added n-butyllithium (50 ml of a 2.5M solution in hexanes, 125 mmol) over 20 minutes maintaining the temperature below −20° C. The resulting suspension was allowed to warm to room temperature overnight. The resulting suspension was filtered and washed with THF (20 ml) then dioxane (20 ml). The solid was removed from the filter pad before all the solvent had been removed by vacuum filtration. Analysis by proton NMR showed a 3:1 ratio of isopropyl:pyridyl groups and that the damp product was 50% 'wet' with THF and dioxane.

(b) Preparation of 6-fluoro-3,4-dimethoxy-2-(2-pyridyl)benzonitrile

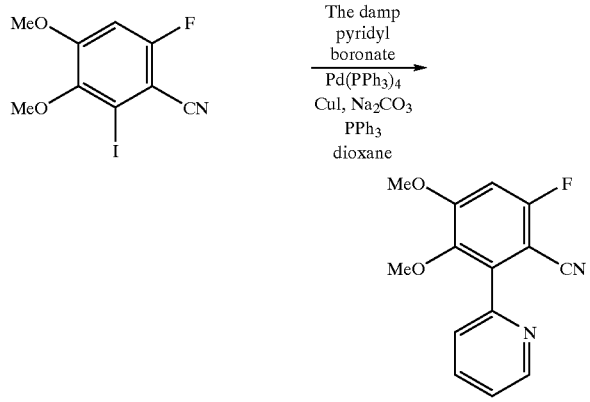

Stirred dioxane (20 ml) at 80° C. was charged with 6-fluoro-2-iodo-3,4-dimethoxybenzonitrile from Example 1(a) (1.0 g, 3.3 mmol), tetrakis(triphenylphosphine) palladium(0) (0.19 g, 0.16 mmol), the pyridyl boronate from step (a) above (6.1 g, estimated to be 9.9 mmol), copper(I) iodide (0.25 g, 1.3 mmol), sodium carbonate (0.69 g, 6.5 mmol) and triphenylphosphine (0.17 g, 0.65 mmol) and the resulting brown slurry heated to reflux and stirred at this temperature overnight. The resulting suspension was cooled to room temperature, ethyl acetate (20 ml) and water (10 ml) added and the resulting mixture filtered through Arbocel™ filter aid. The phases were separated and the aqueous phase extracted with ethyl acetate (2×20 ml). The organic phases were combined, washed with saturated aqueous NaCl and stripped to an oil. Acetonitrile was added and the mixture warmed then cooled. The resulting suspension was filtered to give a solid that was dried in vacuo overnight at 45° C. to give 0.419 of the product (48%).

EXAMPLE 1B

Third Route to 6-fluoro-3,4-dimethoxy-2-(2-pyridyl)benzonitrile (a) Preparation of 6-fluoro-3,4-dimethoxy-2-(2-pyridyl)benzonitrile

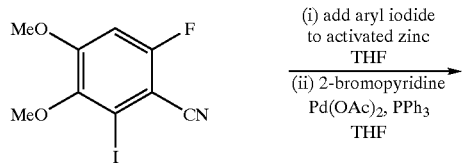

-continued

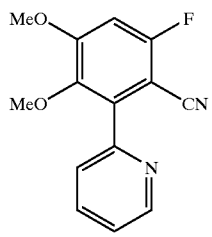

Under nitrogen, to a vigorously stirred suspension of zinc dust (25.5 g, 391 mmol) in anhydrous THF (700 ml) was added chlorotrimethylsilane (10.7 ml, 85 mmol) and the suspension heated to 60° C. After 1 hour at 60° C. the reaction was allowed to cool to 40° C. and a solution of 6-fluoro-2-iodo-3,4-dimethoxybenzonitrile (as prepared in Example 1(a), 100 g, 330 mmol) was added slowly over a period of 20 minutes, keeping the temperature in the range 40° C. to 50° C. The resulting suspension was heated to 60° C. for 1 hour then allowed to cool to room temperature. 2-Bromopyridine (61.8 g, 391 mmol), palladium acetate (0.73 g, 3.3 mmol) and triphenylphosphine (1.71 g, 6.5 mmol) were added and the suspension heated to 60° C. for 1 hour then allowed to cool to room temperature. The reaction was quenched with a 5% aqueous solution of the dipotassium salt of ethylenediaminetetraacetic acid (1 liter), followed by DCM (2 liters) and the resulting mixture stirred for 15 minutes. After this time the mixture was filtered through Arbocel™ filter aid and the pad washed with DCM (100 ml). The phases were separated and the organic phase washed with water (1 liter). The organic phase was distilled and replaced with acetonitrile to give a final volume of 1 liter and the resulting solution left to cool to room temperature overnight. The resulting suspension was filtered and the solid dried in vacuo overnight at 45° C. to give 54.0 g of the title product (67%).

EXAMPLE 1C

Fourth Route to 6-fluoro-3,4-dimethoxy-2-(2-pyridyl)benzonitrile (a) Preparation of 2-bromo-3,4-dimethoxybenzaldehyde

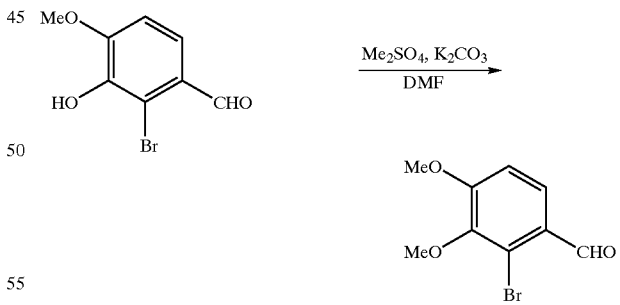

A stirred suspension of 2-bromo-3-hydroxy-4-methoxybenzaldehyde (commercially available, 24 g, 104 mmol) and $K_2CO_3$ (29.4 g, 213 mmol) in DMF (125 ml) was cooled to −10° C. Dimethylsulfate (9.6 ml, 102 mmol) was added, the reaction was warmed to room temperature and stirred overnight. The resulting solution was quenched with water (375 ml) and the resulting suspension stirred overnight. The resulting suspension was filtered and the solid dried in vacuo at 50° C. to give 23.1 g of the subtitle product (91%).

(b) Preparation of 2-bromo-3,4-dimethoxybenzonitrile

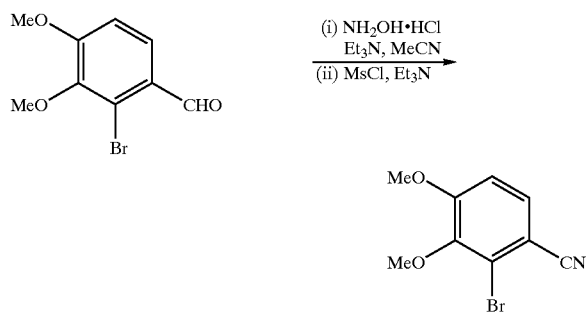

A mixture of hydroxylamine hydrochloride (1.42 g, 20. 4 mmol) and triethylamine (5.7 ml, 40.8 mmol) in acetonitrile (10 ml) was stirred at room temperature for 15 minutes before a solution of 2-bromo-3,4-dimethoxybenzaldehyde (5.0 g, 20.4 mmol) in acetonitrile (40 ml) was added over 40 minutes. The resulting mixture was stirred overnight before a fifth of the resulting solution was charged with methanesulfonyl chloride (0.74 ml, 10 mmol total) and triethylamine (0.6 ml, 4.3 mmol total) portionwise over 6 hours. The mixture was stirred overnight, quenched with water, extracted with ethyl acetate, dried over MgSO$_4$ and concentrated in-vacuo to give 0.90 g of the subtitle product (93%).

(c) Preparation of 2-bromo-3,4-dimethoxy-6-nitrobenzonitrile

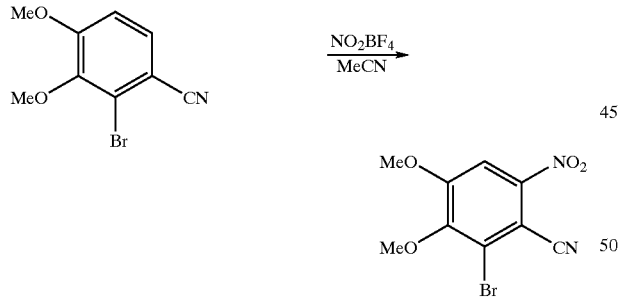

To a stirred solution of 2-bromo-3,4-dimethoxybenzonitrile (prepared according to step (b), 5.77 g, 23.8 mmol) in acetonitrile (58 ml) at 0° C. was added nitronium tetrafluoroborate (5.67 g, 42.9 mmol) portionwise ensuring that the temperature did not rise above 10° C. After stirring for 4 hours in the range 0° C. to 10° C., the reaction was cautiously quenched into 10% aqueous NaHCO$_3$ (66 ml). The resulting suspension was filtered and the solid dried in vacuo overnight to give 5.83 g of the subtitle product (85%).

(d) Preparation of 2-bromo-6-fluoro-3,4-dimethoxybenzonitrile

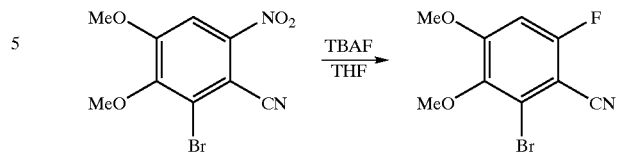

A partially dried solution of tetrabutylammonium flouride (24 ml, 1M in THF stored over 4A sieves) was added to 2-bromo-3,4-dimethoxy-6-nitrobenzonitrile (prepared according to step (c), 1.73 g, 6.02 mmol) with stirring at room temperature. After 1 hour ethyl acetate was added and the mixture washed with 1M aqueous HCl (50 ml). The aqueous wash was extracted with ethyl acetate (50 ml) and the combined organics then washed with aqueous NaHCO$_3$ (50 ml) before being dried over MgSO$_4$ and concentrated in vacuo. The crude residue was recrystallised from toluene:tert-butylmethylether (1:1) to give 1.34 g of the subtitle product (85%).

(e) Preparation of 6-fluoro-3.4-dimethoxy-2-(2-pyridyl)benzonitrile

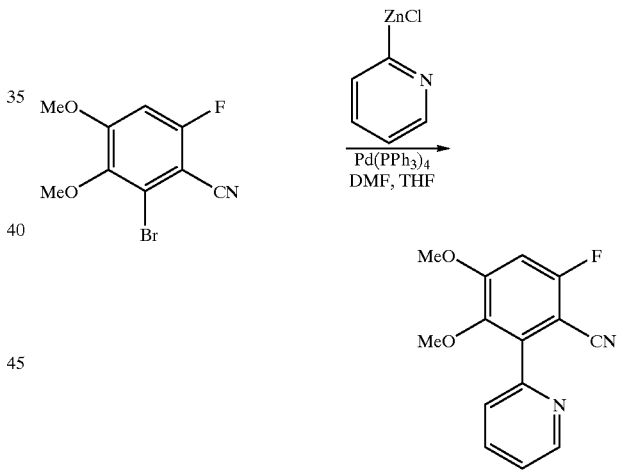

A mixture of pyridyl zinc chloride (max 31.5 mmol, prepared from 2-bromopyridine by bromine to magnesium to zinc exchange) in THF (30 ml) and 2-bromo-6-fluoro-3,4-dimethoxybenzonitrile (prepared according to step (d), 3.30 g, 12.7 mmol) in DMF (75 ml) was charged with tetrakis(triphenylphosphine)palladium(0) (0.59 g, 0.51 mmol), warmed to 98° C. and maintained at this temperature for 15 hours. After this time, the reaction mixture was cooled to room temperature and water (300 ml) added. The resulting mixture was extracted with ethyl acetate (3×150 ml), and the combined organics dried over MgSO$_4$ before being concentrated in vacuo. The crude product was purified on silica gel (eluting with hexane/ethyl acetate [7/3 followed by 1/1] to give 3.1 g of the title product (93%).

EXAMPLE 2

Preparation of N-(2-amidino-1,2,3,4-tetrahydro-5-isoquinolyl)methanesulfonamide

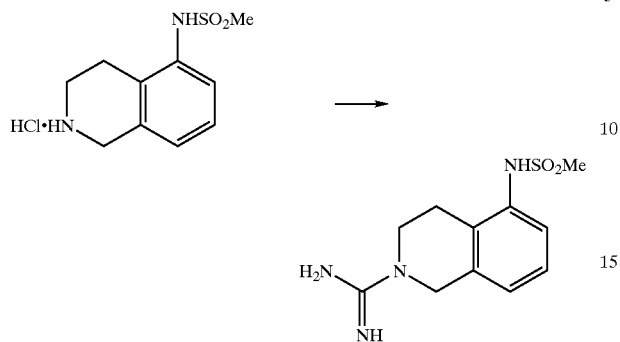

To a stirred suspension of N-(1,2,3,4-tetrahydro-5-isoquinolyl)methanesulfonamide hydrochloride prepared as described in Example 19(b) of WO 98/30560 (100 g, 0.38 mol) and 2-methyl-2-thiopseudourea sulfate (159 g, 0.57 mol) in water (1.5 liter) was added 2N aqueous sodium hydroxide (764 ml, 1.53 mol). The resulting solution was warmed to 80° C. and stirred at this temperature for 6 hours and then left to cool to room temperature overnight. Further 2-methyl-2-thiopseudourea sulfate (27 g, 0.10 mol) and 2N aq. sodium hydroxide (48 ml, 0.10 mol) were charged and the mixture heated at 80° C. for 1 hour. After this time the resulting suspension was cooled to room temperature, filtered, washed with water (1 liter) to give a white solid that was dried in vacuo overnight at 50° C. to give 91.0 g of the title product (89%).

EXAMPLE 2A

Alternative Route to N-(2-amidino-1,2,3,4-tetrahydro-5-isoquinolyl)methanesulfonamide

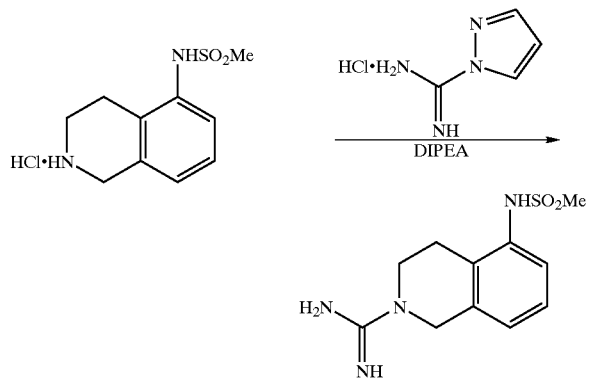

A suspension of N-(1,2,3,4-tetrahydro-5-isoquinolyl)methanesulfonamide hydrochloride obtainable by the method of Example 19(b) of WO 98/30560 (15 g, 69 mmol), 1H-pyrazole-1-carboxamidine hydrochloride (10.0 g, 0.57 mol) and diisopropylethylamine (16.2 g, 125 mmol) in DMF (119 ml) was stirred overnight at room temperature. After this time 2N aqueous sodium hydroxide-was added to adjust to pH 12. The resulting white suspension was stirred for three hours, filtered and the solid dried in vacuo overnight at 45° C. to give 14.5 g of the title product (95%).

EXAMPLE 3

4-Amino-2-(5-methanesulfonamido-1,2,3,4-tetrahydroisoguinol-2-yl)-6,7-dimethoxy-5-(2-pyridyl)quinazoline

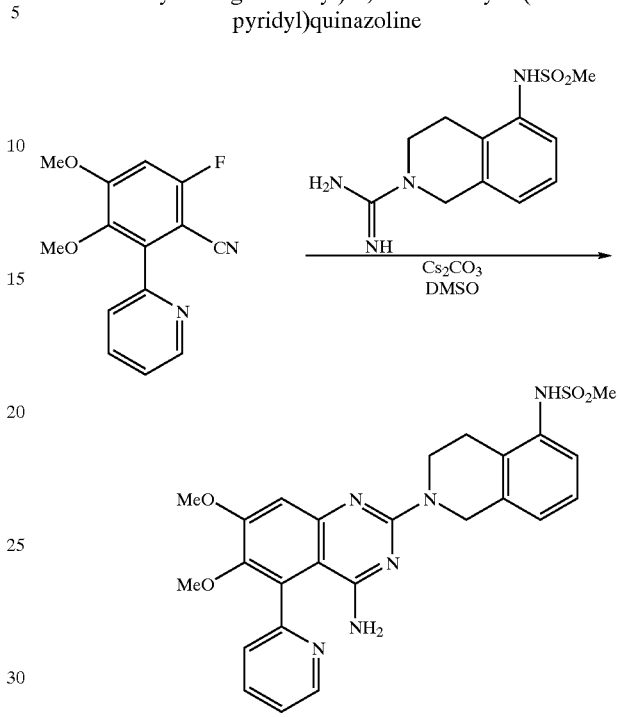

To a 3-necked flask equipped with a mechanical stirrer was charged 6-fluoro-3,4-dimethoxy-2-(2-pyridyl)benzonitrile, (obtainable by the method of Example 1, 50.0 g, 194 mmol), to N-(2-amidino-1,2,3,4-tetrahydro-5-isoquinolyl)methanesulfonamide (obtainable by the method of Example 2, 99.5 g, 371 mmol), $Cs_2CO_3$ (150 g, 416 mmol) and DMSO (150 ml, 3 mlg$^{-1}$). The mixture was slurried at ambient temperature under a $N_2$ atmosphere. The resultant viscous slurry was heated to 94–97° C. for 30 hours then allowed to cool to 40° C. 1N NaOH (700 ml) was added to the reaction and the resultant mixture was stirred for 1 hour at ambient temperature. The mixture was filtered through an Arbocel™ filter aid pad. The filtrate was washed with DCM (250 ml). The aqueous phase was collected and partitioned with DCM (500 ml) and stirred. The two-phase solution was adjusted from pH13 to the range pH10 to pH10.5 by the controlled addition of 5N HCl. The two phases were separated and the organic phase held. The aqueous phase was extracted with DCM (250 ml). The combined organic extracts were distilled and replaced with acetonitrile until all of the DCM was removed. The final solvent volume was adjusted by addition of acetonitrile to 300 ml and this mixture was allowed to cool to ambient temperature. The resulting suspension was filtered and the solid dried in vacuo at 50° C. overnight to yield 56 g of the title product (57%).

The preparation of 4-amino-2-(5-methanesulfonamido-1,2,3,4-tetrahydroisoquinol-2-yl)-6,7-dimethoxy-5-(2-pyridyl)quinazoline according to the above examples is illustrated in the following scheme, which also indicates the Example number of each step and the general formula which covers the relevant compound:

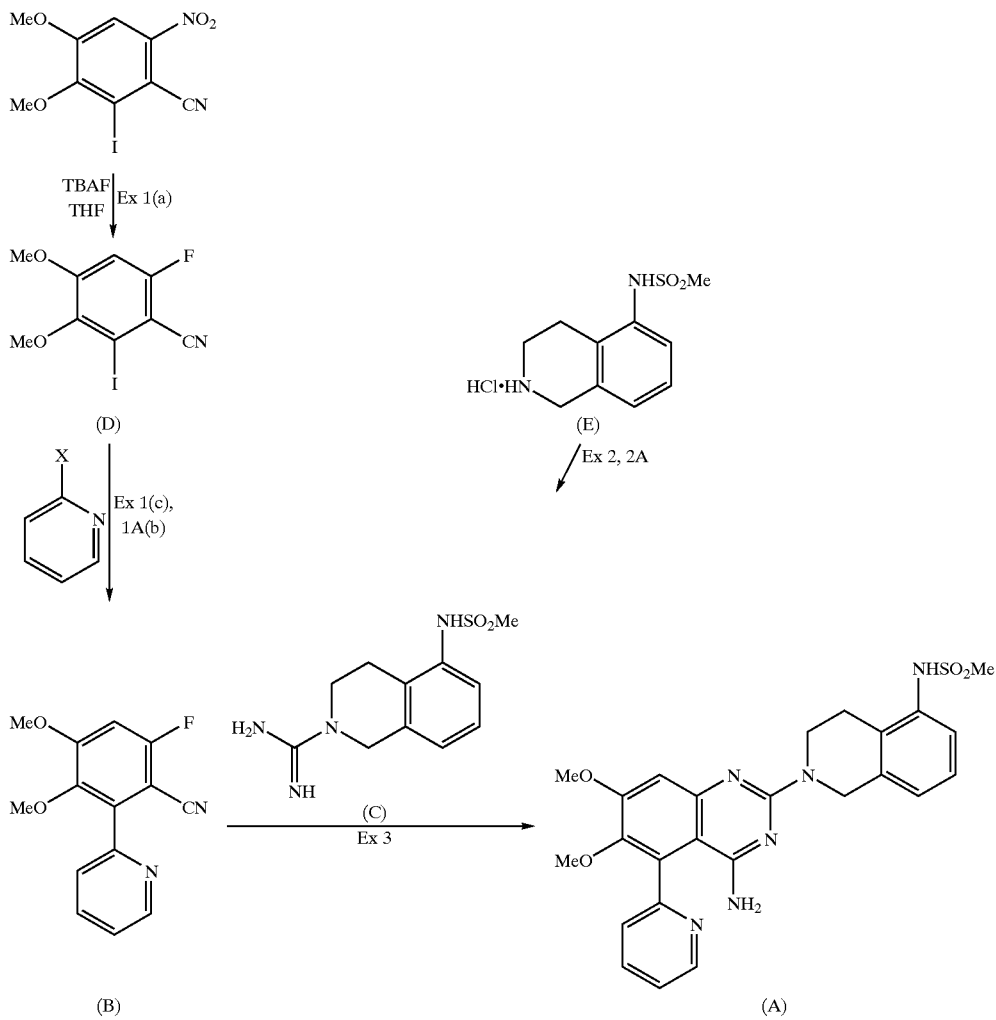

What is claimed is:

1. A process for the production of a compound of formula (A) or a pharmaceutically acceptable salt or solvate thereof:

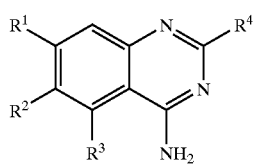

(A)

wherein:
  $R^1$ represents $C_{1-4}$ alkoxy optionally substituted by one or more fluorine atoms;
  $R^2$ represents H or $C_{1-6}$ alkoxy optionally substituted by one or more fluorine atoms;
  $R^3$ represents a 5- or 6-membered heterocyclic ring containing at least one heteroatom selected from N, O and S, the ring being optionally substituted by one or more groups selected from halogen, $C_{1-4}$ alkoxy, $C_{1-4}$ alkyl and $CF_3$;
  $R^4$ is a 4-, 5-, 6-, or 7-membered heterocyclic ring containing a nitrogen heteroatom, the ring being optionally fused to a benzene ring, the ring system as a whole being optionally substituted by one or more groups independently selected from OH, $C_{1-4}$ alkoxy, $C_{1-4}$ alkyl, halogen, $CONR^7R^8$, $SO_2NR^7R^8$, $(CH_2)_b NR^7R^8$, and $NHSO_2(C_{1-4}$ alkyl);

the process comprising condensing a compound of formula (B) with a compound of formula (C):

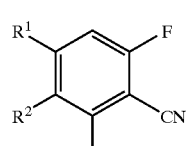

(B)

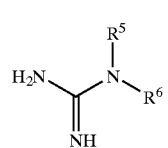

(C)

wherein
  $R^1$ to $R^3$ are as defined above;
  $R^5$ and $R^6$ taken together with the N atom to which they are attached represent a 4-, 5-, 6-, or 7-membered N-containing heterocyclic ring, the ring being optionally fused to a benzene ring, the ring system as a whole being optionally substituted by one or more groups independently selected from OH, $C_{1-4}$ alkoxy, $C_{1-4}$ alkyl, halogen, $CONR^7R^8$, $SO_2NR^7R^8$, $(CH_2)_bNR^7R^8$, and $NHSO_2(C_{1-4}$ alkyl);

$R^7$ and $R^8$ independently represent H or $C_{1-4}$ alkyl, or together with the N atom to which they are attached they may represent a 5- or 6-membered heterocyclic ring containing at least one heteroatom selected from N, O and S; and b represents 0, 1, 2 or 3; and where necessary or desired, converting the resulting compound of formula (A) into a pharmaceutically acceptable salt or solvate, or converting the resulting salt or solvate into a compound of formula (A).

2. A process as claimed in claim 1, wherein $R^1$ represents methoxy.

3. A process as claimed in claim 1, wherein $R^2$ represents methoxy.

4. A process as claimed in claim 1, wherein $R^3$ represents an aromatic ring.

5. A process as claimed in claim 4, wherein $R^3$ represents pyridinyl, pyrimidinyl, thienyl, furanyl or oxazolyl.

6. A process as claimed in claim 5, wherein $R^3$ represents 2-pyridinyl or 2-pyrimidinyl.

7. A process as claimed in claim 1, wherein $R^4$ represents a saturated 6-membered N-containing ring which is fused to an optionally substituted benzene ring.

8. A process as claimed in claim 7, wherein $R^4$ represents a tetrahydroisoquinoline ring system.

9. A process as claimed in claim 8, wherein $R^4$ is 5-methylsulfonylamino-tetrahydroisoquinoline.

10. A process as claimed in claim 1, wherein the reaction is carried out in a polar aprotic solvent.

11. A process as claimed in claim 10, wherein the polar aprotic solvent is dimethylsulfoxide.

12. A process as claimed in claim 1, wherein the reaction is carried out in the presence of a base.

13. A process as claimed in claim 12, wherein the base is an alkali metal carbonate.

14. A process as claimed in claim 13, wherein the base is caesium carbonate.

15. A process as claimed in claim 1, wherein the product is 4-amino-6,7-dimethoxy-2-(5-methanesulfonamido-1, 2, 3, 4-tetrahydoisoquinol-2-yl)-5-(2-pyridyl) quinazoline.

* * * * *